United States Patent [19]

Tobol et al.

[11] 4,143,144
[45] Mar. 6, 1979

[54] ETHERS OF 4-HALOMETHYLPYRIDINES

[75] Inventors: Helen K. Tobol, Concord, Calif.; Robert L. Noveroske, Midland, Mich.

[73] Assignee: The Dow Chemical Company, Midland, Mich.

[21] Appl. No.: 889,303

[22] Filed: Mar. 23, 1978

[51] Int. Cl.² .................. C07D 213/64; A01N 9/22
[52] U.S. Cl. .................... 424/263; 546/269; 546/283; 546/284; 546/290
[58] Field of Search .......... 260/294.8 D, 297 R, 260/297 B; 424/263

[56]  References Cited
U.S. PATENT DOCUMENTS

| 3,244,722 | 4/1966 | Johnston et al. | 250/294.8 |
| 3,317,542 | 5/1967 | Haszeldine et al. | 260/295 |
| 3,983,238 | 9/1976 | Morisawa et al. | 424/266 |
| 4,062,962 | 12/1977 | Noveroske | 424/263 |

Primary Examiner—Henry R. Jiles
Assistant Examiner—R. W. Ramsuer
Attorney, Agent, or Firm—S. Preston Jones; C. Kenneth Bjork

[57] ABSTRACT

Compounds are prepared which correspond to the formula

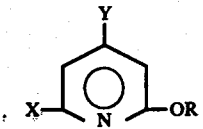

wherein Y represents trichloromethyl, dichloromethyl or dichlorofluoromethyl; X represents chloro, bromo, fluoro, alkoxy of 1 to 4 carbon atoms or OR; each R independently represents —(CH$_2$)$_3$OR$^2$,

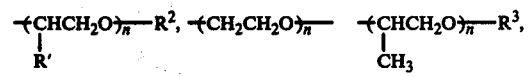

2-furanylmethyl, 5-alkyl-2-furanylmethyl, tetrahydro-3-furyl, tetrahydro-2-furylmethyl, tetrahydro-2-pyranylmethyl, 2-thiophenemethyl, 2,3-dihydrobenzodioxin-2-ylmethyl or 2,2-dimethyl-1,3-dioxolan-4-ylmethyl; each R' independently represents hydrogen or methyl; R$^2$ represents hydrogen, alkyl of 1 to 4 carbon atoms or phenyl; R$^3$ represents hydrogen or alkyl of 1 to 4 carbon atoms and each n independently represents an integer of from 1 to 12. These compounds and compositions containing them have been found to be useful as agronomic fungicides, especially useful and valuable for the control of soil-borne plant disease organisms which attack the roots of plants.

38 Claims, No Drawings

ETHERS OF 4-HALOMETHYLPYRIDINES

DESCRIPTION OF THE PRIOR ART

In U.S. Pat. No. 3,244,722, issued Apr. 5, 1966, there are described and claimed, among other related compounds, those corresponding to the formula

[Structure: pyridine with CCl$_3$, OR, and Cl substituents]

wherein R is alkyl of 1 to 18 carbon atoms or lower alkenyl.

Exemplary compounds listed in this patent include 2-chloro-4-methoxy-6-(trichloromethyl)pyridine, 2-chloro-6-methoxy-4-(trichloromethyl)pyridine, 5-chloro-2-methoxy-4-(trichloromethyl)pyridine, and 3-chloro-2-methoxy-4-(trichloromethyl)pyridine. As reported in this patent, various compounds disclosed therein are useful as herbicides; various other compounds are useful in the control of pest fish and aquatic insects; and other compounds are taught to be useful as insecticides and anthelmintic agents for warm-blooded animals.

In U.S. Pat. No. 4,062,962, issued Dec. 13, 1977, a select group of the compounds taught in U.S. Pat. No. 3,244,722 are taught as fungicides for the control of soil-borne plant disease organisms which attack the roots of plants.

In U.S. Pat. No. 3,983,238, issued Sept. 28, 1976, there are described and claimed compounds having anticoccidal activity. These compounds are of the formula:

[Structure: pyridine with R$_1$O, CH$_2$OR$_2$, and CH$_3$ substituents]

wherein R$_1$ and R$_2$ are each hydrogen, aliphatic acyl, aromatic acyl or heterocyclic acyl with at least R$_1$ or R$_2$ being heterocyclic acyl.

Other related known prior art includes U.S. Pat. No. 3,317,542, issued May 2, 1967 which is directed to compounds of the formula

[Structure: pyridine with X, F, F, Z, Y substituents]

wherein X, Y and Z may be the same or different and each represents a list of groups including alkoxy and methyl. The utility of these compounds is not set forth.

SUMMARY OF THE INVENTION

The present invention is directed to compounds corresponding to the formula

[Structure: pyridine with X, Y, and OR substituents]

In this and succeeding formulae, Y represents trichloromethyl, dichloromethyl or dichlorofluoromethyl; X represents chloro, bromo, fluoro, alkoxy of 1 to 4 carbon atoms or OR; R represents:

—(CH$_2$)$_3$OR$^2$,

—(CHCH$_2$O)$_{\overline{n}}$R$^2$,
   |
   R'

—(CH$_2$CH$_2$O)$_{\overline{n}}$—(CHCH$_2$O)$_{\overline{n}}$R$^3$,
                        |
                        CH$_3$ 5-substituted-2-furanylmethyl $\left( -CH_2-\left[\begin{array}{c}O\\ \end{array}\right]-R^3 \right)$, tetrahydro-3-furyl $\left( \left[\begin{array}{c}O\\ H\end{array}\right] \right)$, tetrahydro-2-furylmethyl $\left( -CH_2-\left[\begin{array}{c}O\\ H\end{array}\right] \right)$, tetrahydro-2-pyranylmethyl $\left( -CH_2-\left[\begin{array}{c}O\\ H\end{array}\right] \right)$, 2-thiophene methyl $\left( -CH_2-\left[\begin{array}{c}S\\ \end{array}\right] \right)$, 2,3-dihydrobenzodioxin-2-ylmethyl $\left( -CH_2-\left[\begin{array}{c}O\\ H\\ O\end{array}\right] \right)$, or 2,2-dimthyl-1,3-dioxolan-4-ylmethyl $\left( -CH_2-\left[\begin{array}{c}O\\ H\end{array}\right]\begin{array}{c}CH_3\\ -CH_3\\ O\end{array} \right)$;

each R' independently represents hydrogen or methyl; R$^2$ represents hydrogen, alkyl of 1 to 4 carbon atoms or phenyl; R$^3$ represents hydrogen or alkyl of 1 to 4 carbon atoms; and each n independently represents an integer of from 1 to 12.

In the present specification and claims, the term "alkyl" designates a straight or branched chain saturated aliphatic hydrocarbon group containing from 1 to 4 carbon atoms, inclusive, such as, for example, methyl, ethyl, propyl, isopropyl or butyl. The term "alkoxy" as employed in the present specification and claims designates straight or branched chain alkoxy groups of 1 to 4 carbon atoms, inclusive, such as, for example, methoxy, ethoxy, propoxy, isopropoxy, butoxy, secondary-butoxy and tertiary butoxy.

In the present specification and claims, the formula

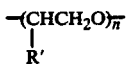

is employed to designate both oxyethylene and oxypropylene groups and when n is more than 1, the formula designates the residue of a homopolymer of each alkylene oxide.

In the present specification and claims, the formula

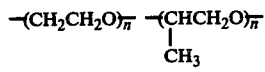

is employed to designate the residue of copolymers containing at least one oxyethylene and at least oxypropylene group and when each n is more than 1, the formula designates the residue of copolymers of ethylene and propylene oxide. It is preferred that the oxyethylene and oxypropylene groups are arranged in random fashion along the oxyalkylene chain.

The pyridine compounds of the present invention are crystalline solids or oils and are of low solubility in water and of moderate solubility in common organic solvents.

The pyridine compounds of the present invention and compositions containing said compounds have been found useful, as agronomic fungicides, especially useful and valuable for the control of soil-borne plant root disease organisms.

The compounds of the present invention can be prepared by a variety of methods. In the preparation of compounds wherein X is chloro, bromo, fluoro or OR, the compounds can be prepared by the reaction of an appropriate halomethyl substituted halopyridine reactant with an alkali metal salt of an appropriate glycol ether, polyglycol or oxygen or sulfur containing heterocyclic in the presence of a reaction medium (the alkali metal salt can be preformed or formed in situ). This reaction can be represented as follows:

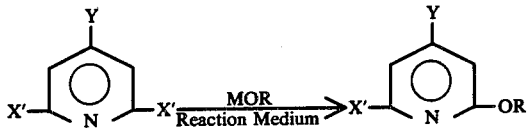

In the above reaction representation, no attempt has been made to present a balanced equation. In addition, X' represents chloro, bromo or fluoro; Y, X and R are as hereinbefore defined and M represents sodium, potassium, lithium, or cesium.

In carrying out the above reaction, the appropriate halomethyl substituted halopyridine reactant is mixed with the alkali metal salt of an appropriate glycol ether, polyglycol or oxygen or sulfur containing heterocyclic and the reaction medium and the mixture refluxed until the reaction is complete. The reaction is usually complete in from about 0.5 to about 18 hours, depending upon the specific reactants and solvents employed.

After the completion of the reaction, the reaction mixture is usually diluted with water and extracted with a solvent such as methylene chloride, petroleum ether, hexane or toluene. The extract is thereafter usually washed with water, dried, and filtered, if desired, and the solvent and any residual alcoholic by-products present are removed by evaporation or other conventional separatory procedures. The product is thereafter recovered and, if desired, can be purified by various conventional techniques such as crystallization and/or recrystallization from solvents such as, for example, methanol, hexane or toluene or by distillation depending upon whether the product is a solid or oil.

In carrying out the above preparations, the amounts of the reactants employed is not critical as some of the desired product is formed with any amounts. However, since the reaction consumes the reactants in equimolar proportions (1 molar equivalent of the alkali metal salt reactant per halogen atom to be reacted), these amounts for the most part should be employed. It has, however, been found, that when preparing compounds wherein both halogens are reacted or wherein the last halogen is being reacted, that an increase in the yield of the desired product can be obtained by employing an excess of the alkali metal salt reactant. Therefore, it is preferred to employ from about 1.5 to about 6 molar equivalents or more of the alkali metal salt reactant per halogen atom to be reacted.

Representative reaction medias useful for carrying out the above preparations include, for example, dimethylsulfoxide, dimethylformamide, toluene or the alkanols and alkenols of the same carbon content as the alkoxides or alkenoxides employed for the reaction (this includes the glycols and heterocyclic alcohols).

In the preparation of compounds wherein X is alkoxy, the compound can be prepared by the reaction of an appropriate halomethyl-2-ether substituted 6-halopyridine reactant with an alkali metal alkoxide in the presence of a reaction medium. This reaction can be represented as follows:

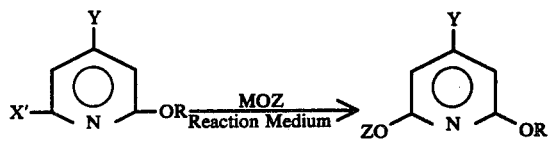

In the above reaction representation, no attempt has been made to present a balanced equation. In addition, X', Y, M and OR are as hereinbefore defined. Additionally, Z represents alkyl of 1 to 4 carbon atoms. In the above procedure, the reaction proceeds as outlined hereinabove and the product is separated in the same manner.

Since many 4-halomethyl-2-halo-6-alkoxy pyridines are known as taught in U.S. Pat. No. 3,244,722, it is within the scope of the present invention to employ such compounds as starting materials in the preparation of compounds of the present invention wherein X is alkoxy of 1 to 4 carbon atoms. In such procedures, this reactant is mixed with the desired MOR reactant as hereinabove set forth, and the reaction proceeds as outlined hereinbefore.

This reaction can be represented as follows:

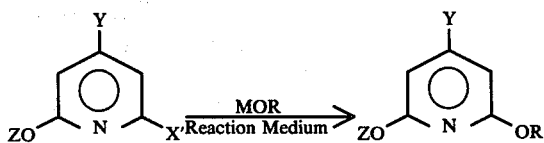

In the above representation, no attempt has been made to present a balanced equation. In addition, X', Y, Z, M and OR are as hereinbefore defined.

When carrying out the methods of preparation as outlined hereinabove, it is within the scope of this invention to convert the halomethyl group of an existing product to a different halomethyl group thereby forming a different halomethyl compound. For example, a compound of the present invention containing a trichloromethyl group can be dehalogenated, with a dehalogenation agent such as, for example, stannous chloride or zinc metal in the presence of concentrated hydrochloric acid and a solvent, to the dichloromethyl analog under conventional conditions; or with antimony trifluoride in the presence of chlorine gas, to dichlorofluoromethyl analog.

In such procedure, a solution of the trichloromethyl substituted pyridine compound in a solvent such as acetone, acetic acid or toluene is contacted and refluxed with a solution containing an excess of the dehalogenation agent dissolved in one of the above solvents. The reaction is usually straight forward and is completed in from about 1 to about 4 hours.

PREPARATION OF STARTING MATERIALS 2,6-Dichloro-4-(dichloromethyl)pyridine

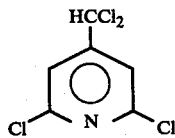

To a solution of 73 grams (0.275 mole) of 2,6-dichloro-4-(trichloromethyl)pyridine dissolved in 125 milliliters of acetone was added a solution of 108 grams (0.48 mole) of stannous chloride hydrate and 40 milliliters of concentrated hydrochloric acid in 500 milliliters of acetone. The mixture was refluxed for 2.0 hours. The solid which formed was separated by filtration and three fourths of the solvent was thereafter removed by evaporation. The remainder of the reaction mixture was diluted with water and the oil phase which formed, removed by extraction with hexane. The 2,6-dichloro-4-(dichloromethyl)pyridine product was dried and recovered from the solvent by evaporation of the solvent. The product had a boiling point of 123°–126° C. at 1.6 millimeters of mercury.

2,6-Dichloro-4-(dichlorofluoromethyl)pyridine

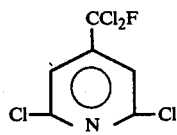

A mixture containing 138.5 grams (0.522 mole) of 2,6-dichloro-4-(trichloromethyl)pyridine and 34 grams (0.187 mole) of antimony trifluoride was heated to 80°–84° C. and maintained under agitation for 23 minutes. During this step, a slow stream of chlorine gas was passed over the surface of the reaction mixture. The reaction mixture was steam distilled and the crude 2,6-dichloro-4-(dichlorofluoromethyl)pyridine was purified by fractionation. The product had a boiling point of 74°–76° C. at 1.0 millimeter of mercury.

The 2,6-dibromo or difluoro counterparts of the above dichloro compounds can be prepared by conventional halogen exchange. They can also be prepared by employing the 2,6-dibromo(or difluoro)-4-(trichloromethyl)-pyridine as the starting material in the above procedure.

The compounds employed as starting materials in the present invention which correspond to the formula:

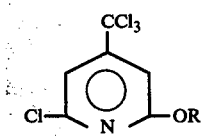

wherein R is as hereinbefore defined, are all known in the art and can be purchased commercially or they can be prepared as taught in U.S. Pat. No. 3,244,722. The compounds can be prepared by reacting 2,6-dichloro-4-(trichloromethyl)pyridine with an alkali metal salt of the appropriate hydroxy (alcohol) compound in a solvent at a temperature of from about 60° to about 120° C. for about 0.5 to 10 hours.

The compounds employed as starting materials of the present invention which correspond to the formula:

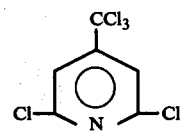

can be prepared as taught in U.S. Pat. No. 3,244,722. This patent teaches that the compounds may be prepared by contacting an appropriate methylpyridine and hydrogen chloride at temperatures of about 50° C. to produce a liquid methylpyridine hydrochloride composition, thereafter passing chlorine gas through the liquid mixture at temperatures of from about 95° to about 110° C. while irradiating the reaction mixture and thereafter fractionally distilling the liquid mixture. The compounds may also be prepared by rapidly mixing in the vapor phase chlorine, an appropriate methylpyridine and an inert diluent such as a perchlorinated hydrocarbon during a brief contact time at temperatures of from about 400° C. to about 490° C. and thereafter cooling to precipitate the desired starting material or fractionally distilling to recover the desired starting material.

The compounds employed as starting materials which correspond to the formula:

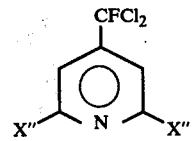

wherein each X" is chloro, bromo or fluoro can be prepared employing the procedures taught by McBee et al., 2nd Eng. Chem. 39, pages 389–391 (1947) (see Chem. Abstracts, Vol. 41, pages 3461d). In this procedure an appropriate 2,6-dihalo-4-(trichloromethyl)pyridine is treated with HF in an autoclave at temperatures up to 300° C.

It should be further noted that while there are many procedures for preparing the starting materials, they all can be prepared employing the procedures outlined in U.S. Pat. No. 3,244,722 or modifications thereof or combinations of any of the procedures outlined hereinabove.

The compounds of the present invention and formulation containing them have been found to be useful as agronomic fungicides, especially valuable for the control of soil-borne plant root disease organisms which attack the roots of plants. In accordance with the present invention, a method for protecting plants, which are in soil containing soil-borne plant root disease organisms, from attack by said organisms, is provided, which comprises contacting plants or plant parts with a non-phytotoxic plant protecting amount of at least one of the compounds set forth hereinabove or with a composition (formulation) containing at least one of the compounds.

One of the advantages of the present method is that by the mode of action of the active toxicant, plant root diseases can be eliminated from infected plants and non-infected plants can be protected from attack.

The present method also offers a practical advantage in that there is no need to employ the additional time and labor required by conventional pre-plant sterilization with soil fumigants.

A further practical advantage of the present method is that the active compounds or toxicants are used in amounts which are the equivalent of ounces of the active ingredient on a per acre basis as against the conventional soil fumigation practices which require pounds and hundreds of pounds of active material per acre.

In the present specification and claims, the term "plant part" is employed to designate all parts of a plant and includes seeds, the underground portion, i.e., bulbs, stolons, tubers, rhizomes, ratoons, corms, the root system, hereinafter commonly referred to as root, and the above-ground portion, i.e., the crown, stalk, stem, foliage or leaf system, fruit or flower.

In the present specification and claims, the term "systemic" defines the translocation of the active compound employed in the present method through the plant whereby they selectively accumulate principally in the underground portions of the plant. The following illustrative example will further the understanding of the term "systemic" as used herein. If the active compounds are applied to seeds, accumulation of the active compound is found mainly in the underground system of the germinating seed; if applied to storage organs (bulbs, stolons, tubers, rhizomes, ratoons or corms), the active compound will absorb into the plant tissue and upon active growth following dormancy, the compound will be found mainly in the below-ground portion of the growing plant; if applied to the above-ground portions of the plant, the active compounds downwardly translocate and principally accumulate in the underground system; and application of the active compound adjacent the underground portions of the plant gives remarkably fast protection by the compound, due to the proximity of the point of application to the area of chemical accumulation, and to the fact there is mainly no translocation away from the underground system.

Compositions containing one or more of the active compounds of the present invention have been found to be very effective in the control of plant root disease in plants either before or after the plant has been attacked by soil-borne plant root disease organisms.

Representative soil-borne plant root disease organisms which attack the below-ground portion of plants, i.e., the root system and which are controlled by the present method include Verticillium, Fusarium, Rhizoctonia, Phytophthora, Pythium, Thielaviopsis, Aphanomyces and gram-negative bacteria such as Pseudomonas.

Control of soil-borne plant disease by the present invention is achieved, for example, in cereal crops such as corn, wheat, barley, rye, oats, rice and sorghum; vegetable crops such as tomatoes, peppers, lettuce, onions, cabbage, broccoli, squash, cucumbers, cauliflower, etc.; legumes such as peanuts, soybeans, beans, peas and alfalfa; root crops such as turnips, beets, carrots, white potatoes, sweet potatoes and yams; fiber crops such as cotton, flax and hemp; fruit crops such as apples, bananas, cantaloupes, cherries, dates, figs, grapes, pineapples, grapefruit, lemons, limes, oranges, peaches, pears, plums, strawberries and watermelon; oil crops such as castorbean, copra, olives, palms, rubber and sunflower; stimulants such as cocoa, coffee, tea and tobacco; sugar crops such as sugar cane and sugar beets; turf including bent grass and blue grass, rye and fescue; ornamentals such as chrysanthemums, zinnias, carnations, lilies, violets, petunias, marigolds, philodendrons, schefflera, dracaena, wax plants, jade plant, ivy, ferns, rubber plants, cactus and dieffenbachia; woody ornamentals such as pines, roses, rhododendrons, azaleas, boxwoods, spruces and the like. While the above lists a variety of crop plants which may be treated by the practice of the present invention, it is to be understood that the present method is not restricted to the above list of crop plants.

Generally in the actual practice of the method of the present invention, a plant protecting amount of the active toxicant compounds can be applied to the plant or plant part by a variety of convenient procedures. Such procedures include soil incorporation whereby compositions containing the active toxicant are mechanically mixed with the soil; applied to the surface of the soil and thereafter dragged, disced or rototilled into the soil; or transported into the soil with a liquid carrier such as by injection, spraying or irrigation. Additionally, a plant protecting amount of the active toxicant compounds can be employed in sprays, gels or coatings for above-ground applications or drenched onto the soil surface. In additional application methods, the active toxicant can be applied by vapor transfer; added in liquid or solid composition to hydroponic operations; seed treatment operations and by conventional plant part coating operations or other techniques known to those skilled in the art. The only limitation upon the mode of applications employed is that it must be one which will ultimately allow the toxicant to come in contact with plants or plant parts.

The exact dosage of the active toxicant employed can be varied depending upon the specific plant, its stage of development, hardiness, the mode of application and its growth media. Generally, the active ingredient should be present in an amount equivalent to from about 50 micrograms to about 140 grams or more per plant on a per plant basis. Translating this into conventional application rates, this amount is equivalent to from about 0.0005 pound to about 10 pounds or more of the active ingredient on a per acre basis, as chemical available to the plant.

It will be appreciated that on a per plant basis, seed treatment of small seeded plant species such as grasses, carrots, and the like will actually require much smaller amounts than 50 micrograms per plant. Generally, rates in the range of onethirty-second to about 8 ounces per 100 pounds of seeds will be optimum for seed treatment among the diversity of plant species. For practices such as conventional tobacco transplant treatment or in-furrow soil treatment of plants such as soybeans at seeding and the like, an amount of active toxicant approximately equal to 8 to about 32 milligrams would be utilized on a per plant basis.

Larger amounts of the active ingredient may advantageously be applied when treatments are employed which distribute the material throughout the soil. For example, when the active ingredient is applied as an at-plant row treatment or as an early or mid-season post-plant side dress treatment, those amounts of chemical not proximal to plant roots are essentially unavailable to the plant and therefore not effective as set forth hereinabove. In such practices, the amount of the active ingredient employed needs to be increased to rates as high as about 20 pounds per acre or higher to assure that the requisite effective quantity of active ingredient is made available to the plants.

The present invention can be carried out by employing the pyridine compounds directly, either singly or in combination. However, the present invention also embraces the employment of liquids, dusts, wettable powders, granules or encapsulated compositions containing at least one of said compounds as active ingredient. In such usage, the compound or compounds can be modified with one or more of a plurality of additaments or adjuvants including inert solvents, inert liquid carriers and/or surface active dispersing agents and coarsely or finely-divided inert solids. The augmented compositions are also adapted to be employed as concentrates and subsequently diluted with additional inert carrier to produce other compositions in the form of dusts, sprays, granules, washes or drenches. In compositions where the adjuvant is a coarsely or finely-divided solid, a surface active agent or the combination of a surface active agent and a liquid additament, the adjuvant cooperates with the active component so as to facilitate the invention. Whether the composition is employed in liquid, wettable powder, gel, wax, jelly, dust, granule, or encapsulated form, the active compound will normally be present in an amount of from 2 to 98 percent by weight of the total composition.

In the preparation of dust, or wettable powder compositions, the toxicant products can be compounded with any of the finely-divided solids, such as pyrophyllite, talc, chalk, gypsum, fuller's earth, bentonite attapulgite, modified clays, starch, casein, gluten and the like. In such operations, the finely-divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, organic carriers such as ground corn cobs, walnut hulls, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent and water. Preferred dispersing agents which can be employed in these compositions, are oil-soluble materials including non-ionic emulsifiers such as the condensation products of alkylene oxides with the inorganic acids, polyoxyethylene derivatives or sorbitan esters, complex ether alcohols, alkyl phenols and the like. Also, oil-soluble ionic emulsifying agents such as mahogany soaps can be used. Suitable inert organic liquids which can be employed in the compositions include petroleum oils and distillates, toluene, liquid halohydrocarbons, synthetic organic oils and vegetable oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an inert organic liquid such as acetone, methylene chloride, chlorobenzene and petroleum distillates. The preferred inert organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° F. Also desirable are those petroleum fractions with higher boiling points which can leave residues due to their low vapor pressure, provided they are low in aromatic content such as paraffinic and isoparaffinic oils which are of low phytotoxicity potential. The proportion of the compounds of this invention employed in a suitable solvent may vary from about 2 to about 50 percent or higher. Additionally, the active components can be compounded with water or petroleum jellies to prepare the viscous or semi-solid treating compositions.

The expression "soil" is employed herein in its broadest sense to be inclusive of all conventional "soils", as defined in Webster's New International Dictionary, Second Edition, unabridged, published in 1937, G. C. Merriam Co., Springfield, Massachusetts. Thus, the term refers to any substance or medium in which plants may take root and grow, and is intended to include not only earth, but also compost, manure, muck, sand, synthetic growth mediums such as vermiculite and pearlite and the like, adapted to support plant growth. In this context, hydroponic growth mediums are also included.

DESCRIPTION OF SOME PREFERRED EMBODIMENTS FOR USE

In order that the method of the present invention may be more fully understood, the following examplesare given to illustrate the manner by which the method can be practiced but, as such, should not be construed as limitations upon the overall scope of the same.

EXAMPLE I

Soil infected with the tobacco black shank pathogen *Phytophthora parasitica* var. nicotianeae was uniformly mixed and placed in 6-inch pots. To said pots were transplanted six week old tobacco seedlings of the "402" variety which had been grown in pathogen free soil. Test dispersions of 2,6-bis-(2-methoxyethoxy)-4-

(trichloromethyl)pyridine were prepared by dissolving 0.48 grams of the chemical in 2-cubic centimeters (cc) acetone containing 20 milligrams (mg) of Tween 85 emulsifier (a proprietary material of Imperial Chemical Industries, U.S., which is a polyoxyethylene (20) sorbitan trioleate) and thereafter diluting the solution with water to prepare dispersions containing 300, 150, and 75 parts by weight of the compound per million parts of the ultimate dispersion. Thereafter, the test dispersions were employed to treat separate pots containing the seedling by pouring 100 cubic centimeters of each of the dispersions onto the soil, assuring root contact with sufficient chemical. Additional pots were treated with an aqueous acetone solution containing no toxicant to serve as controls. After treatments, the plants were maintained under conditions conducive for good plant growth. Three weeks after treatment, the plants were examined for disease control. The results of this examination are set forth below in Table I.

TABLE I

| Active Compound Employed | Application Rate in ppm* | Percent Control of *Phytophthora parasitica* in Tobacco Seedlings 3 weeks |
|---|---|---|
| 2,6-Bis(2-methoxyethoxy)-4-(trichloromethyl)pyridine | 300 | 66 |
|  | 150 | 33 |
|  | 75 | 0 |
| Acetone Control | — | 0 |

*Equivalent to dosage rate of 1.0, 0.5 and 0.25 pounds of active compound per acre assuming a planting rate of 7,000 plants per acre.

EXAMPLE II

Soil infected with the tobacco black shank pathogen *Phytophthora parasitica* var. nicotianeae was uniformly mixed and placed in 6-inch pots. To said pots were transplanted six week old tobacco seedlings of the "402" variety which had been grown in pathogen free soil. Test dispersions of the hereinafter set forth compounds were prepared by dissolving 0.225 grams of the chemical in 1-cubic centimeter (cc) of acetone containing 10 milligrams (mg) of Tween 85 emulsifier and thereafter diluting the solution with water to prepare dispersions containing predetermined amounts of the test chemical. Thereafter, the test dispersions were employed to treat separate pots containing the seedling by pouring 100 cubic centimeters of each of the test dispersions onto the soil, assuring root contact with sufficient chemical. The test compounds were present in amounts equivalent to 12 and 6 ounces of the active compound per acre. Additional pots were treated with an aqueous acetone solution containing no toxicant to serve as controls. After treatments, the plants were maintained under conditions conducive for good plant growth. Nineteen days after treatment, the plants were examined for disease control. The results of this examination are set forth below in Table II.

TABLE II

| | Percent Kill and Control of *Phytophthora parasitica* 19 Days After Treatment at Indicated Dosage in Ounces Per Acre | |
|---|---|---|
| Compound Tested | 12 | 6 |
| 2-Chloro-6-(2-methoxyethoxy)-4-(trichloromethyl)pyridine | 100 | 100 |
| 2-Chloro-6-(2-methoxyethoxy)-4-(dichloromethyl)pyridine | 66 | 66 |
| 2-Chloro-6-(2-(2-methoxyethoxy)ethoxy)-4-(trichloromethyl)pyridine | 66 | 0 |
| 2-Chloro-6-(2-butoxyethoxy)-4-(trichloromethyl)pyridine | 66 | 66 |
| 2-Chloro-6-(2-methoxy-1-methylethoxy)-4-(trichloromethyl)pyridine | 66 | 33 |
| 2-Chloro-6-(2-ethoxyethoxy)-4-(trichloromethyl)pyridine | 100 | 100 |
| Control | 0 | 0 |

EXAMPLE III

Acetone dispersions were prepared by admixing predetermined amounts of one of the hereinafter set forth compounds with predetermined amounts of acetone, water and surfactant.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying one ounce of one of the test mixtures directly onto the soil surface and seeds in the pots to give dosages equivalent to 0.25, 0.5 and 1.0 pounds per acre applied as an in-furrow treatment, wherein a 1-inch band of a crop with a 36-inch row spacing is treated. After the acetone had evaporated, the soil in the pots was capped with a layer of sterile soil. Additional pots were also prepared as above to serve as controls and sprayed with a no-toxicant containing acetone-water-surfactant solution. The pots were thereafter maintained under conditions conducive to both plant growth and disease development. Sixteen days after treatment, the pots were examined to determine the amount of disease control, as evidenced by the number of plants surviving. The results of the examination are set forth below in Table III.

TABLE III

| Compound | Number of Plants of Twenty Surviving at Indicated Dosage Equivalent Pounds per Acre in-furrow | | |
|---|---|---|---|
| | 1.00 | 0.50 | 0.25 |
| 2-methoxy-6-(2-methoxyethoxy)-4-(trichloromethyl)-pyridine | 18 | 16 | 16 |
| 2-methoxy-6-(2-butoxyethoxy)-4-(trichloromethyl)-pyridine | 13 | 13 | 12 |
| 2,6-Bis(2-butoxyethoxy)-4-(trichloromethyl)-pyridine | 14 | 13 | 14 |
| Control | 3 | 3 | 3 |

EXAMPLE IV

Acetone dispersions were prepared by admixing predetermined amounts of one of the hereinafter set forth compounds with predetermined amounts of acetone, water and surfactant.

Soil infected with the pea root rot disease organism *Aphanomyces euteiches* was uniformly mixed and used to fill 3-inch pots. Five Little Marvel pea seeds were planted in each pot with 4 pots being used per test mixture. The pots were treated by spraying one ounce of one of the test mixtures directly onto the soil surface and seeds in the pots to give dosages equivalent to 0.25, 0.5 and 1.0 pounds per acre applied as an in-furrow treatment, wherein a 1-inch band of a crop with a 36-inch row spacing is treated. After the acetone had evaporated, the soil in the pots was capped with a layer of sterile soil. Additional pots were also prepared as above and sprayed with acetone-water-surfactant solution containing no toxicant to serve as controls. The pots thereafter maintained under conditions conducive to both plant growth and disease development. Two weeks after treatment, the pots were examined to determine the amount of disease control, as evidenced by the number of plants surviving. The results of this examination are set forth below in Table IV.

EXAMPLE V

Acetone dispersions were prepared by admixing predetermined amounts of one of the hereinafter set forth compounds with predetermined amounts of acetone, surfactant and water.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying one ounce of one of the test mixtures directly onto the soil surface and seeds in the pots to give dosages equivalent to 0.25, 0.5 and 1.0 pounds per acre applied as an in-furrow treatment, wherein a 1-inch band of a crop with a 36-inch row spacing is treated. After the acetone had evaporated, the soil in the pots was capped with a layer of sterile soil. Additional pots were also prepared as above and sprayed with acetone-water-surfactant solution containing no toxicant to serve as controls. The pots were thereafter maintained under conditions conducive to both plant growth and disease development. The pots were examined to determine the amount of disease control, as evidenced by the number of plants surviving, afforded over a long time period, namely 26 days and 36 days after treatment. The results of these examinations are set forth below in Table V.

TABLE IV

| Compound | Number of Plants of Twenty Surviving at Indicated Dosage Equivalent Pounds per Acre in-furrow | | |
|---|---|---|---|
| | 1.00 | 0.50 | 0.25 |
| 2-methoxy-6-(2-methoxyethoxy)-4-(trichloromethyl)-pyridine | 18 | 17 | 16 |
| 2-methoxy-6-(2-butoxyethoxy)-4-(trichloromethyl)-pyridine | 16 | 14 | 12 |
| 2,6-bis(2-butoxyethoxy)-4-(trichloromethyl)-pyridine | 14 | 12 | 10 |
| 2-fluoro-6-(2-butoxyethoxy)-4-(trichloromethyl)pyridine | 14 | 13 | 13 |
| 2-bromo-6-(2-methoxyethoxy)-4-(trichloromethyl)-pyridine | 18 | 15 | 13 |
| Control | 2 | 2 | 2 |

TABLE V

| Compound | Number of Plants Surviving of Twenty at Indicated Dosage and Time Period Equivalent Pound per Acre in-furrow | | | | | |
|---|---|---|---|---|---|---|
| | 1.0 | | 0.5 | | 0.25 | |
| | 26 Days | 36 Days | 26 Days | 36 Days | 26 Days | 36 Days |
| 2-methoxy-6-(2-methoxyethoxy)-4-(trichloromethyl)-pyridine | 19 | 19 | 18 | 18 | 18 | 18 |
| 2-methoxy-6-(2-butoxyethoxy)-4-(trichloromethyl)-pyridine | 18 | 18 | 17 | 16 | 17 | 17 |
| 2,6-bis(2-butoxyethoxy)-4-(trichloromethyl)-pyridine | 18 | 18 | 14 | 8 | 11 | 8 |
| 2-fluoro-6-(2-butoxyethoxy)-4-(trichloromethyl)- | | | | | | |

TABLE V-continued

| | Number of Plants Surviving of Twenty at Indicated Dosage and Time Period | | | | | |
|---|---|---|---|---|---|---|
| | Equivalent Pound per Acre in-furrow | | | | | |
| | 1.0 | | 0.5 | | 0.25 | |
| Compound | 26 Days | 36 Days | 26 Days | 36 Days | 26 Days | 36 Days |
| pyridine | 16 | 16 | 18 | 18 | 15 | 15 |
| Control | 4 | 2 | 4 | 2 | 4 | 2 |

EXAMPLE VI

Acetone dispersions were prepared by admixing predetermined amounts of one of the hereinafter set forth compounds with predetermined amounts of acetone, surfactant and water.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying one ounce of one of the text mixtures directly onto the soil surface and seeds in the pots to give dosages equivalent to 0.25, 0.5 and 1.0 pound per acre applied as an in-furrow treatment, wherein a 1-inch band of a crop with a 36-inch row spacing is treated. After the acetone had evaporated, the soil in the pots was capped with an additional layer of the infected soil. Additional pots for use as controls were also prepared as above and sprayed with an acetone-water-surfactant solution containing no toxicant. The pots were thereafter maintained under conditions conducive to both plant growth and disease development. The pots were examined to determine the percent disease control, as evidenced by the number of surviving plants, afforded over a long time period, namely 26 days and 36 days after treatment. The results of these examinations are set forth below in Table VI.

TABLE VI

| | Number of Plants Surviving of Twenty at Indicated Dosage and Time Period | | | | | |
|---|---|---|---|---|---|---|
| | Equivalent Pound per Acre in-furrow | | | | | |
| | 1.0 | | 0.5 | | 0.25 | |
| Compound | 26 Days | 36 Days | 26 Days | 36 Days | 26 Days | 36 Days |
| 2-methoxy-6-(2-methoxyethoxy)-4-(trichloromethyl)-pyridine | 18 | 16 | 19 | 19 | 18 | 15 |
| 2-methoxy-6-(2-butoxyethoxy)-4-(trichloromethyl)-pyridine | 18 | 18 | 18 | 16 | 16 | 17 |
| 2,6-bis(2-butoxyethoxy)-4-(trichloromethyl)-pyridine | 18 | 12 | 16 | 8 | 14 | 6 |
| 2-fluoro-6-(2-butoxyethoxy)-4-(trichloromethyl)-pyridine | 18 | 17 | 17 | 17 | 18 | 18 |
| Control | 3 | 2 | 3 | 2 | 3 | 2 |

EXAMPLE VII

Soil infected with the tobacco black shank pathogen *Phytophthora parasitica* var. nicotianeae was uniformly mixed and placed in 2-inch pots. To said pots were transplanted four week old tobacco seedlings of the "402" variety which had been grown in pathogen free soil. Test dispersions of each of the compounds 2-chloro-6-(2-furanylmethoxy)-4-(trichloromethyl)pyridine, 2-chloro-6-(2-methoxyethoxy)-4-(trichloromethyl)pyridine and 2-(((6-chloro-4-(trichloromethyl)-2-pyridinyl)oxy)methyl)-2,3-dihydro-1,4-benzodioxin were prepared by dissolving the chemicals in acetone and thereafter diluting the solution with water and a surfactant to prepare dispersions containing 100, 33 and 11 parts by weight of each of the compounds per million parts of the ultimate dispersion (ppm). Thereafter, the various test dispersions were employed to treat separate pots containing the seedlings by pouring 50 cubic centimeters of each of the dispersions onto the soil, assuring root contact with sufficient chemical. Additional pots were treated with an aqueous acetone solution containing no toxicant to serve as controls. After treatments, the plants were maintained under conditions conducive for good plant growth and disease development. Five days, 8 days and 13 days after treatment, the plants were examined for disease control. The results of these examinations are set forth below in Table VIII.

TABLE VII

| | Application Rate in PPM | Percent Kill and Control of *Phytophthora parasitica* in Tobacco Seedlings at Indicated Time Period | | |
|---|---|---|---|---|
| | | Days after Treatment | | |
| Active Compound Employed | | 5 | 8 | 13 |
| 2-chloro-6-(2-furanyl-methoxy)-4-(trichloro-methyl)pyridine | 100 | 100 | 100 | 100 |
| | 33 | 100 | 100 | 100 |
| | 11 | 100 | 100 | 75 |
| 2-chloro-6-(2-methoxy-ethoxy)-4-(trichloro-methyl)pyridine | 100 | 25 | 25 | 25 |
| | 33 | 75 | 75 | 75 |
| | 11 | 100 | 100 | 100 |
| 2-(((6-chloro-4-(tri-chloromethyl)-2-pyri-dinyl)oxy)methyl)-2,3--dihydro-1,4-benzodioxin | 100 | 75 | 75 | 75 |
| | 33 | 50 | 50 | 25 |
| | 11 | 0 | 25 | 0 |
| Control | — | — | — | — |

EXAMPLE VIII

Aqueous acetone dispersions were prepared by admixing predetermined amounts of 2-methoxy-6-(2-methoxy-ethoxy)-4-(trichloromethyl)pyridine with predetermined amounts of acetone, surfactant and water.

Soil infected with the soybean root rot disease organism *Phytophthora megasperma* was uniformly mixed and used to fill 3-inch pots. Five soybean seeds of the variety "Harosoy 63" were planted in each pot with 4 pots being used per test mixture. The pots were treated by spraying 5 cubic centimeters of the test mixtures directly onto the soil surface and seeds in the pots to give dosages equivalent to 0.25, 0.5 and 1.0 pound per acre applied as an in-furrow treatment, wherein a 1-inch band of a crop with a 36-inch row spacing is treated. After the acetone had evaporated, the soil in the pots was capped with a layer of sterile soil. Additional pots were also prepared as above and sprayed with an acetone-water-surfactant solution containing no toxicant to serve as controls. The pots were thereafter maintained cant to serve as controls. The plants were thereafter maintained under conditions conducive for good plant growth and disease development. Three, 6 and 14 days after treatment, the plants were examined to determine the percent disease control. The results of this examination are set forth below in Table IX.

TABLE IX

| | Percent Control of *Phytophthora parasitica* in Tobacco Plants at Indicated Dosage and Time period | | | | | | | | |
|---|---|---|---|---|---|---|---|---|---|
| | 100 | | | 33 | | | 11 | | |
| | Dosage in ppm | | | | | | | | |
| Test Compound | 3 Days | 6 Days | 14 Days | 3 Days | 6 Days | 14 Days | 3 Days | 6 Days | 14 Days |
| 2-chloro-6-(2-furanylmethyl)-4-(trichloromethyl)pyridine | 100 | 100 | 100 | 100 | 75 | 75 | 100 | 100 | 50 |
| 2-chloro-6-(2,2-dimethyl-1,3-dioxolan-4-ylmethoxy)-4-(trichloromethyl)-pyridine | 100 | 100 | 100 | 100 | 75 | 75 | 25 | 0 | 0 |
| 2-chloro-6-((tetrahydro-3-furyl)oxy)-4-(trichloromethyl)pyridine | 75 | 50 | 50 | 75 | 50 | 50 | 100 | 50 | 25 |
| 2-chloro-6-(tetrahydro-2-pyranylmethoxy)-4-(trichloromethyl)pyridine | 25 | 25 | 25 | 100 | 25 | 0 | 50 | 0 | 0 |
| 2-chloro-6-(2-(2-methoxyethoxy)ethoxy)-4-(trichloromethyl)pyridine | 50 | 25 | 25 | 100 | 50 | 25 | 0 | 0 | 0 |
| 2-(2-(2-((6-chloro-4-(trichloromethyl)-2-pyridinyl)oxy)ethoxy)ethoxy)ethanol | 50 | 0 | 0 | 0 | 0 | 0 | 0 | 0 | 0 |
| 2-chloro-6-(2-phenoxyethoxy)-4-(trichloromethyl)pyridine | 25 | 0 | 0 | 0 | 0 | 0 | 0 | 0 | 0 |
| Control | 0 | 0 | 0 | 0 | 0 | 0 | 0 | 0 | 0 | under conditions conducive to both plant growth and disease development. Twelve days and 35 days after treatment, the pots were examined to determine the degree of disease control, as evidenced by the number of surviving plants. The results of this examination are set forth below in Table VIII.

TABLE VIII

| | Number of Plants Surviving of Twenty at Indicated Dosage and Time Period | | | | | |
|---|---|---|---|---|---|---|
| | Equivalent Pound per Acre in-furrow | | | | | |
| | 1.0 | | 0.5 | | 0.25 | |
| Test Compound | 13 Days | 35 Days | 13 Days | 35 Days | 13 Days | 35 Days |
| 2-methoxy-6-(2-methoxyethoxy)-4-(trichloromethyl)pyridine | 13 | 9 | 18 | 16 | 16 | 14 |
| Control | 12 | 5 | 12 | 5 | 12 | 5 |

EXAMPLE IX

A study was conducted following the practice of the present invention to determine the effectiveness of drench treatment of the compounds of the present invention in controlling the tobacco black shank pathogen *Phytophthora parasitica* var. nicotianeae in tobacco plants.

Test concentrates were prepared by dissolving a predetermined amount of one of the hereinafter set forth compounds with a predetermined amount of acetone containing a predetermined amount of Tween 85. The final dispersions were prepared by diluting a predetermined amount of the concentrate with a predetermined amount of water. Test dispersions were prepared containing 100, 33 and 11 ppm of each concentrate.

Tobacco plants of the variety "402" were grown in 3-inch pots in sterile soil until they were of the 3 to 4 leaf stage. The plants transplanted into pots filled with soil infected with the tobacco black shank pathogen *Phytophthora parasitica*. This infected soil being a blend of 1 part of a stock culture soil containing said pathogen and 3 parts of a sterile soil. After transplanting, the plants were drenched with 50 cc of one of the test dispersions. At the same time, additional plants are treated with an acetone/Tween 85/water solution containing no toxi-

EXAMPLE X

A study was conducted following the practice of the present invention to determine the effectiveness of drench treatment of the compounds of the present invention in controlling the tobacco black shank pathogen *Phytophthora parasitica* var. nicotianeae in tobacco plants.

Test concentrates were prepared by dissolving a predetermined amount of one of the hereinafter set forth compounds with a predetermined amount of acetone containing a predetermined amount of Tween 85. The final dispersions were prepared by diluting a predetermined amount of the concentrate with a predetermined amount of water. Test dispersions were prepared containing 100, 33 and 11 ppm of each concentrate.

Tobacco plants of the variety "402" were grown in 3-inch pots in sterile soil until they were of the 3 to 4 leaf stage. The plants were transplanted into pots filled with soil infected with the tobacco black shank pathogen *Phytophthora parasicitica*. This infected soil being a blend of 1 part of a stock culture soil containing said pathogen on 4 parts of a soil composed of 75 percent sandy loan and 25 percent peat. After transplanting, the plants were drenched with 50 cc of one of the test dispersions. At the same time, additional plants are treated with an acetone/Tween 85/water solution containing no toxicant to serve as controls. The plants were thereafter maintained under conditions conducive for good plant growth and disease development. Five, 12 and 19 days after treatment, the plants were examined to determine the percent disease control. The results of this examination are set forth below in Table X.

of 1 part of a stock culture soil containing said pathogen on 4 parts of sterile soil. After transplanting, the plants

TABLE X

Percent Control of *Phytophthora parasitica* in Tobacco Plants at Indicated Dosage and Time Period

| | Dosage in ppm | | | | | | | | |
|---|---|---|---|---|---|---|---|---|---|
| | 100 | | | 33 | | | 11 | | |
| Test Compound | 5 Days | 11 Days | 18 Days | 5 Days | 11 Days | 18 Days | 5 Days | 11 Days | 18 Days |
| 2-chloro-6-(2-methoxyethoxy)-4-(trichloromethyl)pyridine | 100 | 100 | 0 | 100 | 100 | 100 | 100 | 75 | 75 |
| butyl-2-chloro-4-(trichloromethyl)-6-pyridinyl hetericpoly(oxyethylene)$_{11.36}$(oxypropylene)$_{8.62}$diether | 100 | 75 | 50 | 75 | 25 | 0 | 25 | 0 | 0 |
| 2-chloro-4-(trichloromethyl)-6-pyridinyl hetericpoly(oxyethylene)$_{11.36}$(oxypropylene)$_{8.62}$ monoether | 75 | 50 | 25 | 25 | 0 | 0 | 0 | 0 | 0 |
| 2-chloro-6-(2-furanylmethoxy)-4-(trichloromethyl)pyridine | 100 | 50 | 50 | 100 | 100 | 100 | 100 | 25 | 25 |
| 2-chloro-6-(tetrahydro-2-furanylmethoxy)-4-(trichloromethyl)pyridine | 75 | 50 | 50 | 100 | 0 | 0 | 75 | 0 | 0 |
| 2-fluoro-6-(2-furanylmethoxy)-4-(trichloromethyl)pyridine | 100 | 75 | 75 | 100 | 50 | 25 | 100 | 50 | 50 |
| 2-fluoro-6-(tetrahydro-2-furanylmethoxy)-4-(trichloromethyl)pyridine | 100 | 0 | 0 | 75 | 0 | 0 | 50 | 0 | 0 |
| 2-fluoro-6-(tetrahydro-2-pyranylmethoxy)4-(trichloromethyl)pyridine | 75 | 25 | 25 | 100 | 0 | 0 | 75 | 0 | 0 |
| 2,6-bis-(tetrahydro-2-furanylmethoxy)-4-(trichloromethyl)pyridine | 100 | 100 | 25 | 0 | 0 | 0 | 0 | 0 | 0 |
| 2,6-bis-(tetrahydro-2-pyranylmethoxy)-4-(trichloromethyl)pyridine | 50 | 0 | 0 | 25 | 0 | 0 | 0 | 0 | 0 |
| 2,6-bis(2-furanylmethoxy)-4-(trichloromethyl)pyridine | 75 | 0 | 0 | 75 | 0 | 0 | 25 | 0 | 0 |
| 2-(((6-chloro-4-(trichloromethyl)-2-pyridinyl)oxy)methyl)-2,3-dihydro-1,4-benzodioxane | 75 | 0 | 0 | 25 | 0 | 0 | 0 | 0 | 0 |
| Control | 0 | 0 | 0 | 0 | 0 | 0 | 0 | 0 | 0 |

EXAMPLE XI

A study was conducted following the practice of the present invention to determine the effectiveness of drench treatment of the compounds of the present invention in controlling the tobacco black shank pathogen *Phytophthora parasitica* var. *nicotianeae* in tobacco plants.

Test concentrates were prepared by dissolving a predetermined amount of one of the hereinafter set forth compounds with a predetermined amount of acetone containing a predetermined amount of Tween 85. The final dispersions were prepared by diluting a predetermined amount of the concentrate with a predetermined amount of water. Test dispersions were prepared containing 100, 33 and 11 ppm of each concentrate.

Tobacco plants of the variety "402" were grown in 3-inch pots in sterile soil until they were of the 3 to 4 leaf stage. The plants were transplanted into pots filled with soil infected with the tobacco black shank pathogen *Phytophthora parasitica*, this infected soil being a blend of 1 part of a stock culture soil containing said pathogen on 4 parts of sterile soil. After transplanting, the plants were drenched with 50 cc of one of the test dispersions. At the same time, additional plants are treated with an acetone/Tween 85/water solution containing no toxicant to serve as controls. The plants were thereafter maintained under conditions conducive for good plant growth and disease development. Five, 8 and 13 days after treatment, the plants were examined to determine the percent disease control. The results of this examination are set forth below in Table XI.

TABLE XI

Percent Control of *Phytophthora parasitica* in Tobacco Plants at Indicated Dosage and Time Period

| | Dosage in ppm | | | | | | | | | | | | | | | | | |
|---|---|---|---|---|---|---|---|---|---|---|---|---|---|---|---|---|---|---|
| | 100 | | | | | | 33 | | | | | | 11 | | | | | |
| | Days | | | | | | | | | | | | | | | | | |
| Test Compound | 5 | 8 | 13 | 19 | 43 | 49 | 5 | 8 | 13 | 19 | 43 | 49 | 5 | 8 | 13 | 19 | 43 | 49 |
| 2-chloro-6-(2-methoxyethoxy)-4-(trichloromethyl)pyridine | 25 | 25 | 25 | 25 | 25 | 0 | 75 | 75 | 75 | 75 | 0 | 0 | 100 | 100 | 100 | 75 | 0 | 0 |
| 2-chloro-6-(2-furanylmethoxy)-4-(trichloromethyl)pyridine | 100 | 100 | 100 | 100 | 100 | 100 | 100 | 100 | 100 | 100 | 100 | 75 | 100 | 75 | 75 | 75 | 0 | 0 |
| 2-(((6-chloro-4-trichloromethyl)-2-pyridinyl)oxy)methyl)-2,3-dihydro-1,4-benzodioxane | 75 | 50 | 0 | 0 | 0 | 0 | 75 | 50 | 25 | 0 | 0 | 0 | 75 | 25 | 0 | 0 | 0 | 0 |
| Control | 0 | 0 | 0 | 0 | 0 | 0 | 0 | 0 | 0 | 0 | 0 | 0 | 0 | 0 | 0 | 0 | 0 | 0 |

EXAMPLE XII

Acetone dispersions were prepared by admixing predetermined amounts of 2-chloro-6-(2-furanylmethoxy)-4-(trichloromethyl)pyridine with predetermined amounts of acetone.

Soil infected with the bean root rot disease organism *Fusarium solani* was uniformly mixed and used to fill 7 × 15-inch trays. Twenty bean seeds of the variety "Earthy Gallatin" were planted in two 15-inch rows in said trays with 2 trays being used per test mixture. The trays were treated by spraying 2 cc of one of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conductive to both plant growth and disease development. Ten, 29 and 60 days after treatment, the trays were examined to determine the amount of disease control, as evidenced by the number of plants surviving. The results of this examination are set forth below in Table XII.

TABLE XII

| Test Compound | Number of Plants of Forty Surviving at Indicated Dosage and Time Period | | | | | |
|---|---|---|---|---|---|---|
| | Equivalent Pound per Acre in-furrow | | | | | |
| | 1.0 | | | 0.5 | | |
| | 10 Days | 29 Days | 60 Days | 10 Days | 29 Days | 60 Days |
| 2-chloro-6-(2-furanylmethoxy)-4-(trichloromethyl)pyridine | 34 | 26 | 6 | 33 | 27 | 10 |
| Control | 16 | 14 | 1 | 16 | 14 | 1 |

EXAMPLE XIII

A study was conducted following the practice of the present invention to determine the effectiveness of foliar treatment of the compounds of the present invention in controlling the tobacco black shank pathogen *Phytophthora parasitica* var. nicotianeae in tobacco plants.

Test concentrates were prepared by dissolving a predetermined amount of one of the hereinafter set forth compounds with a predetermined amount of acetone containing a predetermined amount of Tween 85. The final dispersions were prepared by diluting a predetermined amount of the concentrate with a predetermined amount of water. Test dispersions were prepared containing 100, 33 and 11 ppm of each concentrate.

Tobacco plants of the variety "402" were grown in 3-inch pots in sterile soil until they were of the 3 to 4 leaf stage. The plants transplanted into pots filled with soil infected with the tobacco black shank pathogen *Phytophthora parasitica*. This infected soil being a blend of 1 part of a stock culture soil containing said pathogen and 3 parts of a sterile soil. After transplanting, the plants were drenched with 50 cc of one of the test dispersions. At the same time, additional plants are treated with an acetone/Tween 85/water solution to serve as controls.

The plants were thereafter maintained under conditions conductive for good plant growth and disease development. Three days after treatment, the plants were examined to determine the present disease control. The results of this examination are set forth below in Table XIII.

TABLE XIII

| Test Compound | Percent Control of *Phytophthora parasitica* in Tobacco Plants at Indicated Dosage Three Days After Treatment | | |
|---|---|---|---|
| | Dosage in ppm | | |
| | 100 | 33 | 11 |
| 2-chloro-6-(2-furanylmethoxy)-4-(trichloromethyl)pyridine | 50 | 75 | 100 |
| 2-chloro-6-(2,2-dimethyl-1,3-dioxolan-4-ylmethoxy)-4-(trichloromethyl)pyridine | 75 | 100 | 0 |
| 2-chloro-6-((tetrahydro-3-furyl)oxy)-4-(trichloromethyl)pyridine | 75 | 50 | 50 |
| 2-chloro-6-(tetrahydro-2-pyranylmethoxy)-4-(trichloromethyl)pyridine | 50 | 0 | 0 |
| 2-chloro-6-((tetrahydro-2-furanyl)methoxy)-4-(trichloromethyl)pyridine | 50 | 100 | 75 |
| Control | 0 | 0 | 0 |

EXAMPLE XIV

Acetone dispersions were prepared by admixing a predetermined amount of one of the hereinafter set forth compounds with a predetermined amount of acetone.

Soil infected with the soybean root rot organism *Phytophthora megasperma* was prepared by admixing sterile sandy loam soil with soil infected with the above organism in a 2:1 ratio. The soil mixture was uniformly mixed and used to fill 8 × 30-inch trays. Twenty soybean seeds of the variety "Harosoy 63" were planted in two 30-inch rows in said trays with 2 trays being used per test mixture. The trays were treated by spraying 2 cc of one of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Ten, 15, 27, 31 and 33 days after treatment, the trays were examined to determine the amount of disease control, as evidenced by the number of plants surviving. The results of this examination are set forth below in Table XIV.

TABLE XIV

| Test Compound | Number of Plants of Forty Surviving at Indicated Dosage and Time Period | | | | | | | | | |
|---|---|---|---|---|---|---|---|---|---|---|
| | Equivalent Pounds per Acre in-furrow | | | | | | | | | |
| | 1.0 | | | | | 0.5 | | | | |
| | 10 Days | 15 Days | 27 Days | 31 Days | 33 Days | 10 Days | 15 Days | 27 Days | 31 Days | 33 Days |
| 2-chloro-6-(2-furanylmethoxy)-4-(trichloromethyl)pyridine | 40 | 40 | 39 | 31 | 6 | 39 | 38 | 33 | 32 | 6 |
| 2-chloro-6-(2,2-dimethyl-1,3-dioxolan-4-ylmethoxy)-4-(trichloromethyl)pyridine | — | — | — | — | — | 15 | 9 | 3 | 2 | 0 |
| 2-chloro-6-((tetrahydro-3-furyl)oxy)-4-(trichloromethyl)pyridine | — | — | — | — | — | 20 | 24 | 14 | 13 | 5 |
| 2-chloro-6-(tetrahydro-2-pyranylmethoxy)-4-(trichloromethyl)pyridine | — | — | — | — | — | 24 | 23 | 5 | 2 | 2 |
| 2-chloro-6-((tetrahydro-2-furanyl)methoxy)-4-(trichloromethyl)pyridine | — | — | — | — | — | 25 | 29 | 24 | 22 | 13 |
| 2-chloro-4-(trichloromethyl)-6-pyridinyl-hetericpoly(oxyethylene)$_{11.36}$(oxypropylene)- | | | | | | | | | | |

TABLE XIV-continued

| | Number of Plants of Forty Surviving at Indicated Dosage and Time Period | | | | | | | | | |
|---|---|---|---|---|---|---|---|---|---|---|
| | Equivalent Pounds per Acre in-furrow | | | | | | | | | |
| | 1.0 | | | | | 0.5 | | | | |
| Test Compound | 10 Days | 15 Days | 27 Days | 31 Days | 33 Days | 10 Days | 15 Days | 27 Days | 31 Days | 33 Days |
| $8.62$ monoether | — | — | — | — | — | 22 | 25 | 13 | 8 | 5 |
| Control | 15 | 7 | 3 | 2 | 1 | 15 | 7 | 3 | 2 | 1 |

EXAMPLE XV

Acetone dispersions were prepared by admixing a predetermined amount of one of the hereinafter set forth compounds with a predetermined amount of acetone.

Soil infected with the soybean root rot organism *Phytophthora megasperma* was prepared by admixing equal portions of sterile sandy loam soil with soil infected with the above organism and Michigan peat. The soil mixture was uniformly mixed and used to fill 8 × 30-inch trays. Twenty soybean seeds of the variety "Harosoy 63" were planted in two 30-inch rows in said trays with 2 trays being used per test mixture. The trays were treated by spraying 2 cc of one of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Ten, 15, 27, 31 and 33 days after treatment, the trays were examined to determine the amount of disease control, as evidenced by the number of plants surviving. The results of this examination are set forth below in Table XV.

EXAMPLE XVI

Acetone dispersions were prepared by admixing a predetermined amount of one of the hereinafter set forth compounds with a predetermined amount of acetone.

Soil infected with the soybean root rot organism *Phytophthora megasperma* was prepared by admixing sterile sandy loam soil with soil infected with the above organism in a 2:1 ratio. The soil mixture was uniformly mixed and used to fill 7 × 15-inch trays. Twenty soybean seeds of the variety "Harosoy 63" were planted in two 15-inch rows in said trays with 2 trays being used per test mixture. The trays were treated by spraying 2 cc of one of the test mixture, per row, directly onto the soil surface in the trays to give dosages equivalent to 0.5 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Nine, 16 and 22 days after treatment, the trays were examined to determine the amount of disease control, as evidenced by the number of plants surviving. The results of this examination are set forth below in Table XVI.

TABLE XV

| | Number of Plants of Forty Surviving at Indicated Dosage and Time Period | | | | | | | | | |
|---|---|---|---|---|---|---|---|---|---|---|
| | Equivalent Pounds per Acre in-furrow | | | | | | | | | |
| | 1.0 | | | | | 0.5 | | | | |
| Test Compound | 10 Days | 15 Days | 27 Days | 31 Days | 33 Days | 10 Days | 15 Days | 27 Days | 31 Days | 33 Days |
| 2-chloro-6-(2-furanylmethoxy)-4-(trichloromethyl)pyridine | 38 | 36 | 22 | 22 | 8 | 39 | 37 | 25 | 24 | 12 |
| 2-chloro-6-(2,2-dimethyl-1,3-dioxolan-4-ylmethoxy)-4-(trichloromethyl)pyridine | — | — | — | — | — | 9 | 5 | 3 | 2 | 1 |
| 2-chloro-6-((tetrahydro-3-furyl)oxy)-4-(trichloromethyl)pyridine | — | — | — | — | — | 12 | 16 | 10 | 9 | 4 |
| 2-chloro-6-(tetrahydro-2-pyranylmethoxy)-4-(trichloromethyl)pyridine | — | — | — | — | — | 15 | 10 | 5 | 5 | 5 |
| 2-chloro-6-((tetrahydro-2-furanyl)methoxy)-4-(trichloromethyl)pyridine | — | — | — | — | — | 21 | 22 | 9 | 10 | 5 |
| 2-chloro-4-(trichloromethyl)-6-pyridinyl-hetericpoly(oxyethylene)$_{11.36}$(oxypropylene)$_{8.62}$ monoether | — | — | — | — | — | 11 | 8 | 6 | 5 | 3 |
| Control | 11 | 9 | 7 | 6 | 4 | 11 | 9 | 7 | 6 | 4 |

TABLE XVI

| | Number of Plants of Forty Surviving at Indicated Doseage of 0.5 Pounds per Acre in-furrow and at Indicated Time Period | | |
|---|---|---|---|
| Test Compound | 9 Days | 16 Days | 22 Days |
| 2-chloro-6-(5-methyl-2-furanylmethoxy)-4-(trichloromethyl)pyridine | 38 | 34 | 34 |
| 2-chloro-6-(2-thiophenemethoxy)-4-(trichloromethyl)pyridine | 40 | 38 | 35 |
| 2-chloro-6-(2-furanylmethoxy)-4-(dichlorofluoromethyl)pyridine | 39 | 38 | 38 |
| 2-chloro-4-(trichloromethyl)-6-pyridinyl hetericpoly(oxyethylene$_{9.80}$(oxypropylene)- | | | |

TABLE XVI-continued

| Test Compound | Number of Plants of Forty Surviving at Indicated Doseage of 0.5 Pounds per Acre in-furrow and at Indicated Time Period | | |
|---|---|---|---|
| | 9 Days | 16 Days | 22 Days |
| $_{2.47}$ monoether | 40 | 30 | 19 |
| 2-chloro-4-(trichloromethyl)-6-pyridinyl hetericpoly (oxyethylene)$_{2.95}$(oxypropylene)-$_{6.72}$ monoether | 39 | 25 | 17 |
| 2-chloro-4-(trichloromethyl)-6-pyridinyl hetericpoly(oxyethylene)$_{6.00}$(oxypropylene)-$_{4.56}$ monoether | 39 | 37 | 36 |
| Control | 39 | 18 | 8 |

EXAMPLE XVII

Acetone dilutions were prepared by dissolving 2-chloro-6-(2-furanylmethoxy)-4-(trichloromethyl)pyridine in predetermined amounts with predetermined amounts of acetone. One milliliter aliquots of each dilution were applied equally to 1-ounce seedlots of pea seeds of the variety "Little Marvel". This application procedure resulted in an equivalent to treating 100 pounds of seeds at a dilution rate of 1, 2, 4 and 8 ounces of active compound. Forty seeds from each treatment were thereafter planted in 7 × 15-inch trays of soil containing the root rot disease organism, *Aphanomyces euteiches*. Forty additional seeds treated with acetone containing no toxicant were also planted to serve as controls. After planting, the trays containing the seeds were watered and placed in a greenhouse under conditions conducive to good plant growth and to disease development. Eleven, 22 and 33 days after treatment, the trays were thereafter examined to determine the percent kill and control of the disease organism from each treatment as evidenced by the number of surviving plants. The results of this examination are set forth below in Table XVII.

EXAMPLE XVIII

Acetone dispersions were prepared by admixing a predetermined amount of one of the hereinafter set forth compounds with a predetermined amount of acetone.

Soil infected with the pea root rot organism *Aphanomyces euteiches* was prepared by admixing 2 parts of sterile sandy loam soil with 1 part of soil infected with the above organism. The soil mixture was uniformly mixed and used to fill 8 × 30-inch trays. Twenty pea seeds of the variety "Green Giant 81005" were planted in two 30-inch rows in said trays with 2 trays being used per test mixture. The trays were treated by spraying 4 cc of one of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Twelve, 30 and 44 days after treatment, the trays were examined to determine the amount of disease control, as evidenced by the number of plants surviving. The results of this examination are set forth below in Table XVIII.

TABLE XVII

| Test Compound | Dosage in Ounces of Active Compounds per 100 Pounds of Seeds | Number of Plants of Forty Surviving at Indicated Dosage and at Indicated Time Period | | |
|---|---|---|---|---|
| | | 11 Days | 22 Days | 33 Days |
| 2,6-Dimethoxy-4-(trichloromethyl)pyridine | 1.0 | 33 | 16 | 15 |
| | 2.0 | 33 | 15 | 6 |
| | 4.0 | 33 | 18 | 8 |
| | 8.0 | 33 | 16 | 4 |
| Control | — | 17 | 10 | 4 |

TABLE XVIII

| Test Compound | Number of Plants of Forty Surviving at Indicated Dosage Rate and Time Period | | | | | |
|---|---|---|---|---|---|---|
| | Equivalent Pounds per Acre in-furrow | | | | | |
| | 1.0 | | | 0.5 | | |
| | 12 Days | 30 Days | 44 Days | 12 Days | 30 Days | 44 Days |
| 2-chloro-6-(2-furanylmethoxy)-4-(trichloromethyl)pyridine | 33 | 13 | 6 | 38 | 20 | 17 |
| 2-chloro-6-(2,2-dimethyl-1,3-dioxolan-4-ylmethoxy)-4-(trichloromethyl)-pyridine | 32 | 21 | 16 | 30 | 20 | 17 |
| 2-chloro-6-((tetrahydro-3-furyl)oxy)-4-(trichloromethyl)pyridine | 29 | 17 | 17 | 34 | 13 | 21 |
| 2-chloro-6-((tetrahydro-2-furanyl)methoxy)-4-(trichloromethyl)pyridine | 32 | 12 | 13 | 37 | 22 | 19 |

TABLE XVIII-continued

| | Number of Plants of Forty Surviving at Indicated Dosage Rate and Time Period | | | | | |
|---|---|---|---|---|---|---|
| | Equivalent Pounds per Acre in-furrow | | | | | |
| | 1.0 | | | 0.5 | | |
| Test Compound | 12 Days | 30 Days | 44 Days | 12 Days | 30 Days | 44 Days |
| Control | 24 | 5 | 3 | 24 | 5 | 3 |

EXAMPLE XIX

Acetone dispersions were prepared by admixing predetermined amounts of 2-chloro-6-(2-furanylmethoxy)-4-(trichloromethyl)pyridine with predetermined amounts of acetone.

Seven by 15-inch trays were filled with sterile sandy loam. Twenty cotton seeds of the variety "SJ-2" and which were infected with the disease organisms *Phythium ultimum* and *Rhizoctonia solani* were planted in two 15-inch rows in said trays with 2 trays being used per test mixture. The trays were treated by spraying 2 cc of the test mixture, per row, directly onto the soil surface in the trays to give dosages equivalent to 0.5 and 1.0 pound of the active material per acre in-furrow based upon a 36-inch row spacing. Additional trays were also prepared as above to serve as controls and were sprayed with acetone containing no toxicant. The trays were thereafter maintained under conditions conducive to both plant growth and disease development. Eleven and 61 days after treatment, the trays were examined to determine the amount of disease control, as evidenced by the number of plants surviving. The results of this examination are set forth below in Table XIX.

TABLE XIX

| | Number of Plants of Forty Surviving at Indicated Dosage and Time Period | | | |
|---|---|---|---|---|
| | Equivalent Pounds per Acre in-furrow | | | |
| | 1.0 | | 0.5 | |
| Test Compound | 11 Days | 61 Days | 11 Days | 61 Days |
| 2-chloro-6-(2-furanylmethoxy)-4-(trichloromethyl)pyridine | 33 | 27 | 33 | 28 |
| Control | 5 | | 5 | |

DESCRIPTION OF SOME PREFERRED EMBODIMENTS FOR COMPOUND PREPARATION

In order that the present invention can be more fully understood, the following examples are given primarily by way of illustration and should not be construed as limitations upon the overall scope of the same.

EXAMPLE XX

2-Chloro-6-(2-methoxyethoxy)-4-(trichloromethyl)-pyridine:

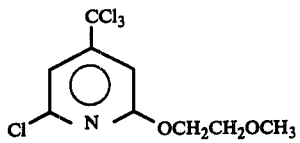

To a solution of 26.54 grams (0.10 mole) of 2,6-dichloro-4-(trichloromethyl)pyridine dissolved in 150 milliliters (ml) of 2-methoxyethanol was added over a 35 minute period, a solution composed of 2.53 grams (0.11 mole) of sodium metal dissolved in 100 ml of 2-methoxyethanol. The mixture was stirred for 5 hours at 65°–75° C. The insoluble by-products were removed by filtration and the 2-methoxyethanol was removed by evaporation under reduced pressure. The resulting oily product was diluted with water and extracted with methylene chloride and dried with sodium sulfate. The methylene chloride was then removed leaving the 2-chloro-6-(2-methoxyethoxy)-4-(trichloromethyl)pyridine as an oil. The product was recovered in a yield of 25.6 grams (84 percent of theoretical) and had a refractive index of n 25/d = 1.5440. Upon analysis, the compound was found to have carbon, hydrogen and nitrogen contents of 35.48, 2.99 and 4.72 percent, respectively, as compared with the theoretical contents of 35.44, 2.97 and 4.59 percent, respectively, as calculated for the above named structure.

EXAMPLE XXI

2-Chloro-6-(2-ethoxyethoxy)-4-(trichloromethyl)-pyridine:

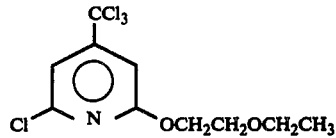

To a solution of 26.54 grams (0.1 mole) of 2,6-dichloro-4-(trichloromethyl)pyridine dissolved in 150 ml of 2-ethoxyethanol was added over a 35 minute period, a solution of 2.53 grams (0.11 mole) of sodium metal dissolved in ~100 ml of 2-ethoxyethanol. The mixture was heated for 5 hours at 65°–75° C. The insoluble by-products were filtered off and the 2-ethoxyethanol was removed by evaporation under reduced pressure. The residue which remained was diluted with water and extracted with methylene chloride and the extract dried with sodium sulfate. The extract was filtered and the methylene chloride evaporated off leaving the 2-chloro-6-(2-ethoxyethoxy)-4-(trichloromethyl)pyridine product as an oil. The product had a refractive index of n 25/d = 1.5395 and was recovered in a yield of 23.8 grams (75 percent of theoretical). Upon analysis, the compound was found to have carbon, hydrogen, nitrogen and chlorine contents of 37.72, 3.25, 4.55 and 44.61 percent, respectively, as compared with the theoretical contents of 37.64, 3.48, 4.39 and 44.45 percent, respectively, as calculated for the above named compound.

EXAMPLE XXII

2-Chloro-6-(2-phenoxyethoxy)-4-(trichloromethyl)-pyridine:

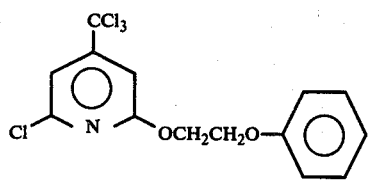

A solution was prepared by dissolving 5.28 grams (0.11 mole) of sodium hydride (as a 50 percent oil mixture) in 15.20 grams (0.11 mole) of 2-phenoxyethanol. To this solution was added, over a 30 minute period, 26.54 grams (0.1 mole) of 2,6-dichloro-4-(trichloromethyl)pyridine. The mixture was heated and refluxed for 4 hours. The reaction mixture was diluted with 700 ml of water and extracted with methylene chloride. The extract was washed with water, dried with sodium sulfate and filtered. The methylene chloride and other volatile impurities were removed by distillation under reduced pressure. The 2-chloro-6-(2-phenoxyethoxy)-4-(trichloromethyl)pyridine product which was recovered distilled at 95° C. under 0.05 mm of pressure. The product was recovered in a yield of 27 grams (73.5 percent of theoretical). The product solidified upon standing at 60°–62° C. Upon analysis, the product was found to have carbon, hydrogen, nitrogen, and chlorine contents of 46.22, 3.15, 3.94 and 37.92 percent, respectively, as compared with the theoretical contents of 45.81, 3.02, 3.82 and 38.64 percent, respectively, calculated for the above named compound.

EXAMPLE XXIII

2-Chloro-4-(trichloromethyl)-6-pyridinyl hetericpoly(oxyethylene)$_{11.36}$(oxypropylene)$_{8.62}$monoether:

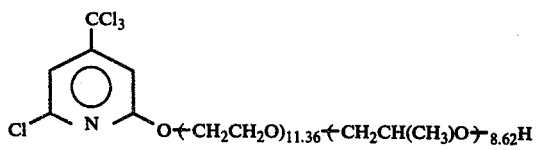

A suspension was prepared by admixing 0.72 grams (0.015 mole) of hexane washed sodium hydride (as a 50 percent oil mixture) with 100 ml of toluene. To this suspension was added 15.0 grams (0.015 mole) of the diol of a heteric 1:1 adduct of ethylene oxide and propylene oxide (HO-CH$_2$CH$_2$O)$_{11.36}$(CH$_2$CH(CH$_3$)O-$_{8.62}$H) dissolved in 40 ml of toluene. The mixture was slowly heated, with stirring, to a temperature of 60° C. over a period of ~70 minutes. To this mixture was added 3.84 grams (0.015 mole) of 2,6-dichloro-4-(trichloromethyl)-pyridine dissolved in 40 ml of toluene. The mixture was heated under reflux conditions for ~4 hours. The toluene was removed by evaporation and the reaction mixture was washed with a small amount of water and the water decanted off. The mixture was thereafter extracted with methylene chloride to remove any water. The mixture was then diluted with additional methylene chloride and washed with a small amount of water and dried over sodium sulfate. The methylene chloride was removed by evaporation under reduced pressure. The 2-chloro-4-(trichloromethyl)-6-pyridinyl heteric-poly(oxyethylene)$_{11.36}$(oxypropylene)$_{8.62}$ monoether product was recovered in a yield of 8 grams (43.7 percent of theoretical) as a dark amber oil having a refractive index of n 25/d = 1.4839.

EXAMPLE XXIV

Butyl 2-chloro-4-(trichloromethyl)-6-pyridinyl hetericpoly(oxyethylene)$_{11.36}$(oxypropylene)$_{8.62}$ diether:

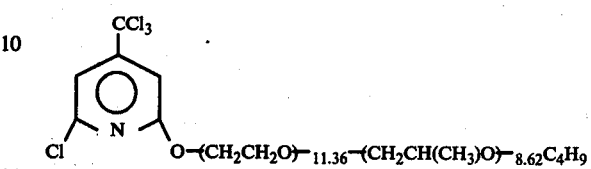

A suspension was prepared by admixing 0.72 grams (0.015 mole) of hexane washed sodium hydride (as a 50 percent oil mixture) with 100 ml of toluene. To this suspension was added 15 grams of a heteric adduct of butanol and ethylene oxide and propylene oxide: (HO-(CH$_2$CH$_2$O)$_{11.36}$(CH$_2$CH(CH$_3$)O)$_{8.62}$C$_4$H$_9$) in 40 ml of toluene. The mixture was heated, with stirring, to a temperature of 65° C. over a period of ~1 hour. To this mixture was added 3.84 grams (0.015 mole) of 2,6-dichloro-4-(trichloromethyl)pyridine dissolved in 40 ml of toluene. The mixture was heated under reflux conditions for ~4 hours. The toluene was removed by evaporation and the residue washed with water and carefully extracted with methylene chloride and the methylene chloride layer dried over sodium sulfate. The methylene chloride was removed by evaporation under reduced pressure. The butyl-2-chloro-4-(trichloromethyl)-6-pyridinyl hetericpoly(oxyethylene)$_{11.36}$(oxypropylene)$_{8.62}$ diether product was recovered in a yield of 11 grams (60 percent of theoretical) as a dark amber oil having a refractive index of n 25/d = 1.4769.

EXAMPLE XXV 2-(((6-Chloro-4-(trichloromethyl)-2-pyridinyl)-oxy)-methyl)-2,3-dihydro-1,4-benzodioxane:

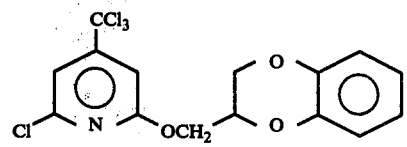

A suspension was prepared by admixing 5.52 grams (0.115 mole) of hexane washed sodium hydride (as a 50 percent oil mixture) with 110 ml of dimethoxyethane. To this suspension was added, over a 5 minute period, 19.11 grams (0.115 mole) of 2-hydroxymethyl-1,4-benzodioxane dissolved in 65 ml of dimethoxyethane. The temperature rose to 40° C. and ~30 minutes later the temperature was at 35° C. At this point, 26.54 grams (0.1 mole) of 2,6-dichloro-4-(trichloromethyl)pyridine was added to the mixture and the mixture refluxed for ~5 hours. The reaction mixture was added to 600 mls of water and the mixture extracted with methylene chloride. The extract was washed with water and dried over sodium sulfate. The methylene chloride was then removed by evaporation. The work-up of the product was continued. The residue was washed with water, extracted with methylene chloride and the extract washed with water and dried over sodium sulfate. The methylene chloride was removed by evaporation and the residue heated to 78° C. at 1.25 millimeters of mercury to remove any dimethoxyethane present. Thereafter the residue, an oily material, was dissolved in 400 mls of ethanol. The mixture was chilled overnight and the oil which settled out was recovered by decantation and the oily product dissolved in 25 mls of pentane. The insolubles were removed by decantation and the pentane removed by evaporation, leaving the 2-(((6-chloro-4-(trichloromethyl)-2-pyridinyl)oxy)methyl)-2,3-dihydro-1,4-benzodioxane product. After drying, the product was recovered as a colorless oil, in a yield of 14 grams. The product had a refractive index of n 25/d = 1.5832 and upon analysis was found to have carbon, hydrogen, nitrogen and chloride contents of 46.75, 3.15, 3.59 and 34.06 percent, respectively, as compared with the theoretical contents of 45.59, 2.81, 3.54 and 35.90 percent, respectively, as calculated for the above named compound. The structure of the product was confirmed by nuclear magnetic resonance spectroscopy.

EXAMPLE XXVI

2-Chloro-6-(2-furanylmethoxy)-4-(trichloromethyl)-pyridine:

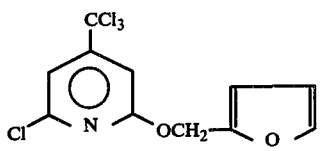

To 24 grams (0.6 mole) of sodium hydroxide dissolved in 120 mls of water, was added 300 mls of 2-(hydroxymethyl)furan and the solution warmed to 50° C. In this mixture was added incrementally over a 20 minute period, 106.15 grams (0.4 mole) of 2,6-dichloro-4-(trichloromethyl)pyridine. The mixture was heated to ~80° C. for ~3.5 hours and thereafter diluted with water and extracted with hexane. The extract was washed with water and the hexane evaporated off leaving ~114 grams (~87 percent of theoretical) of the desired 2-chloro-6-(2-furanylmethoxy)-4-(trichloromethyl)pyridine product. The product, an oil, had a refractive index of n 25/d = 1.5722 and upon analysis was found to have carbon, hydrogen and nitrogen contents of 40.41, 2.21 and 4.21 percent, respectively, as compared with the theoretical contents of 40.40, 2.16 and 4.28 percent, respectively, as calculated for the above named compound.

EXAMPLE XXVII

2-Chloro-6-(2-furanylmethoxy)4-(trichloromethyl)-pyridine:

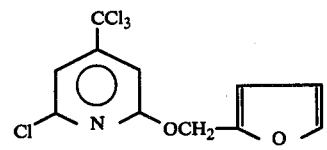

To 5.5 grams (0.115 mole) of hexane washed sodium hydride in 100 mls of dimethoxyethane was added over a 25 minute period, 11.28 grams (0.115 mole) of 2-(hydroxymethyl)furan dissolved in 30 mls of dimethoxyethane. An additional 25 mls of dimethoxyethane was added and the mixture heated to 50° C. for about 10 minutes. To this mixture was added 26.54 grams (0.1 mole) of 2,6-dichloro-4-(trichloromethyl)pyridine dissolved in 100 mls of dimethoxyethane. The mixture was heated under reflux (83° C.) for about 2.5 hours and the reaction mixture added to 600 mls of water and extracted with methylene chloride. The methylene chloride was evaporated from the extract leaving a black oil. This oil was distilled under reduced pressure to obtain 19.05 grams of the desired 2-chloro-6-(2-furanylmethoxy)-4-(trichloromethyl)pyridine product. The product, an oil, had a refractive index of n 25/d = 1.5722 and upon analysis was found to have carbon, hydrogen, nitrogen and chlorine contents of 41.19, 2.50, 4.23 and 42.49 percent, respectively, as compared with the theoretical contents of 40.40, 2.16, 4.28 and 43.37 percent, respectively, as calculated for the above named compound.

By following the general procedures as set forth above and in the examples, the following compounds are prepared.

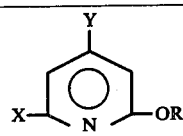

| Y | X | R | Molecular Weight | Refractive Index n 25/d= |
|---|---|---|---|---|
| CCl$_3$ | Cl | —CH$_2$CH$_2$OC$_4$H$_9$ | 347.07 | 1.5247 |
| CCl$_3$ | Br | —CH$_2$CH$_2$OC$_4$H$_9$ | 391.53 | |
| CCl$_3$ | Cl | —CH$_2$CH$_2$OC$_3$H$_7$ | 333.04 | |
| CCl$_3$ | Cl | —CH$_2$CH$_2$OCH(CH$_3$)CH$_3$ | 333.04 | |
| CCl$_3$ | Cl | —CH(CH$_3$)CH$_2$OCH(CH$_3$)CH$_3$ | 347.07 | |
| CCl$_3$ | F | —CH$_2$CH$_2$OC$_4$H$_9$ | 330.62 | 1.5051 |
| CCl$_3$ | Cl | —(CH$_2$CH$_2$O)$_3$H | 379.07 | 1.5536 |
| CCl$_3$ | Cl | —(CH—CH$_2$O)$_2$CH$_3$ | 333.04 | 1.5309 |
| CCl$_3$ | —OCH$_3$ | —CH$_2$CH$_2$CH$_2$OCH$_3$ | 314.60 | |
| CHCl$_2$ | Br | —CH$_2$CH$_2$OCH(CH$_3$)CH$_3$ | 343.05 | |
| CCl$_3$ | Cl | —CH(CH$_3$)CH$_2$OCH$_3$ | 319.02 | 1.5357 |
| CCl$_3$ | F | —CH(CH$_3$)CH$_2$OCH$_3$ | 302.56 | |
| CCl$_3$ | Br | —CH$_2$CH$_2$OCH$_3$ | 337.45 | 1.5602 |
| CCl$_3$ | Cl | —CH(CH$_3$)CH$_2$OC$_4$H$_9$ | 361.10 | |
| CCl$_3$ | —OCH$_3$ | —CH$_2$CH$_2$OC$_4$H$_9$ | 342.65 | 1.5162 |
| CCl$_3$ | —OC$_4$H$_9$ | —CH$_2$CH$_2$OC$_4$H$_9$ | 384.73 | |
| CHCl$_2$ | Cl | —CH$_2$CH$_2$O$\phi$ | 332.62 | |
| CHCl$_2$ | Cl | —CH$_2$CH$_2$OCH$_3$ | 270.54 | 1.5461 |
| CHCl$_2$ | Cl | —CH(CH$_3$)CH$_2$OCH$_3$ | 284.57 | |
| CHCl$_2$ | Cl | —CH$_2$CH$_2$OC$_4$H$_9$ | 312.63 | |
| CHCl$_2$ | F | —CH$_2$CH$_2$OCH$_3$ | 254.09 | |

-continued structure: pyridine ring with Y at 4-position, X at one ortho, OR at other ortho, N in ring

| Y | X | R | Molecular Weight | Refractive Index n 25/d= |
|---|---|---|---|---|
| CCl$_3$ | Cl | —CH$_2$-(tetrahydrofuran-2-yl with H) | 317.00 | 1.5686 |
| CFCl$_2$ | Br | —CH(CH$_3$)CH$_2$OCH$_3$ | 347.16 | |
| CFCl$_2$ | Cl | —CH$_2$CH$_2$Oφ | 350.75 | |
| CFCl$_2$ | F | —CH$_2$CH$_2$OCH(CH$_3$)CH$_3$ | 300.28 | |
| CCl$_3$ | Cl | —CH$_2$-(5-methylfuran-2-yl) | 341.02 | 1.5692 |
| CCl$_3$ | OCH$_3$ | —CH$_2$CH$_2$OCH$_3$ | 300.57 | 1.5339 |
| CCl$_3$ | —OCH$_2$CH$_2$OC$_4$H$_9$ | —CH$_2$CH$_2$OC$_4$H$_9$ | 428.78 | 1.5039 |
| CFCl$_2$ | Cl | —(CH$_2$CH$_2$O)$_3$H | 362.76 | |
| CFCl$_2$ | Cl | —CH(CH$_3$)CH$_2$O(CH$_2$CH$_2$O)$_2$H | 372.75 | |
| CFCl$_2$ | Cl | —(CH$_2$CH$_2$O)$_2$CH$_3$ | 330.72 | |
| CFCl$_2$ | Cl | —(CH$_2$CH$_2$O)$_2$C$_4$H$_9$ | 374.81 | |
| CFCl$_2$ | OC$_2$H$_5$ | CH$_2$CH$_2$OCH$_3$ | 298.29 | |
| CFCl$_2$ | —OCH$_2$CH$_2$OCH$_3$ | —CH$_2$CH$_2$OCH$_3$ | 328.31 | |
| CFCl$_2$ | —OCH$_3$ | —CH$_2$CH$_2$OC$_4$H$_9$ | 326.24 | |
| CFCl$_2$ | Br | —CH$_2$CH$_2$CH$_2$OC$_4$H$_9$ | 389.24 | |
| CFCl$_2$ | F | —CH$_2$CH$_2$CH$_2$OC$_3$H$_7$ | 314.31 | |
| CCl$_3$ | Cl | —CH$_2$CH$_2$CH$_2$OCH$_3$ | 283.56 | 1.5422 |
| CFCl$_2$ | OCH(CH$_3$)CH$_3$ | —CH(CH$_3$)CH$_3$ | 296.31 | |
| CCl$_3$ | OCH$_2$CH$_2$OCH$_3$ | —CH$_2$CH$_2$OCH$_3$ | 344.62 | 1.5213 |
| CCl$_3$ | —OCH$_2$-(tetrahydrofuran,H) | —CH$_2$-(tetrahydrofuran,H) | 396.70 | 1.5415 |
| CCl$_3$ | Cl | —CH$_2$-(dioxolane with C(CH$_3$)$_2$,H) | 343.04 | 1.5362 |
| CCl$_3$ | F | —CH$_2$-(tetrahydrofuran-2-yl,H) | 313.57 | 1.5297 |
| CCl$_3$ | Cl | —CH$_2$-(tetrahydrofuran-2-yl,H) | 330.02 | 1.5572 |
| CHCl$_2$ | Cl | —CH$_2$-(tetrahydrofuran-2-yl,H) | 295.57 | |
| CCl$_3$ | F | —CH$_2$-(furan-2-yl) | 310.54 | 1.5450 |
| CFCl$_2$ | Cl | —CH$_2$-(furan-2-yl) | 310.68 | 1.5465 |
| CFCl$_2$ | OC$_4$H$_9$ | —CH$_2$-(furan-2-yl) | 348.35 | |
| CCl$_3$ | —OCH$_2$-(furan-2-yl) | —CH$_2$-(furan-2-yl) | 390.65 | 1.5650 |
| CCl$_3$ | —O—(CH$_2$CH$_2$O)$_{12}$H | —(CH$_2$CH$_2$O)$_{12}$H | ~1200 | |
| CCl$_3$ | —O—(CH(CH$_3$)CH$_2$O)$_{12}$CH$_3$ | —(CH$_2$CH$_2$O)$_{12}$CH$_3$ | ~1400 | |
| CHCl$_2$ | Br | —CH$_2$CH$_2$OCH(CH$_3$)CH$_3$ | 343.05 | |
| CHCl$_2$ | —OCH$_3$ | —(CH$_2$CH$_2$O)$_2$CH$_3$ | 310.18 | |
| CHCl$_2$ | Cl | —CH(CH$_3$)CH$_2$OCH$_3$ | 284.57 | |
| CCl$_3$ | F | —CH$_2$-(tetrahydropyran-2-yl,H) | 328.60 | 1.5264 |
| CCl$_3$ | Cl | —CH$_2$-(tetrahydropyran-2-yl,H) | 345.05 | 1.5532 |
| CCl$_3$ | —OCH$_2$-(tetrahydropyran-2-yl,H) | —CH$_2$-(tetrahydropyran-2-yl,H) | 392.76 | 1.5390 |

-continued

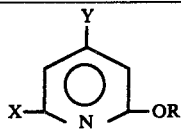

| Y | X | R | Molecular Weight | Refractive Index n 25/d= |
|---|---|---|---|---|
| CCl₃ | Cl | —CH₂—[thiophene] | 343.06 | 1.6019 |
| CCl₃ | —OCH₂—[thiophene] | —CH₂—[thiophene] | 420.77 | 1.6120 |
| CCl₃ | Cl | —(CH₂CH₂O)₂.₉₅—(CH₂CH(CH₃)O)₆.₇₂H | ~767 | 1.4810 |
| CCl₃ | Cl | —(CH₂CH₂O)₉.₈—(CH₂CH(CH₃)O)₂.₄₇H | ~820 | 1.4941 |
| CCl₃ | Cl | —(CH₂CH₂O)₆.₀—(CH₂CH(CH₃)O)₄.₅₆H | ~776 | 1.4800 |

What is claimed is:

1. A compound corresponding to the formula:

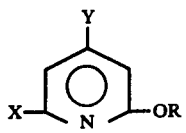

wherein Y represents trichloromethyl, dichloromethyl or dichlorofluoromethyl; X represents chloro, bromo, fluoro, alkoxy of 1 to 4 carbon atoms or OR; R represents:

—(CH₂)₃OR²,

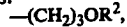

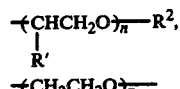

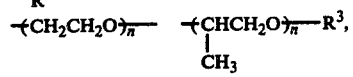

5-substituted-2-furanylmethyl 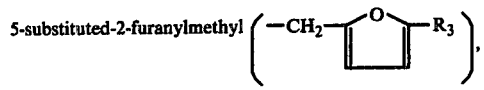, tetrahydro-3-furyl 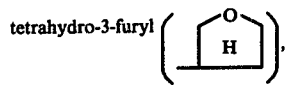, tetrahydro-2-furylmethyl 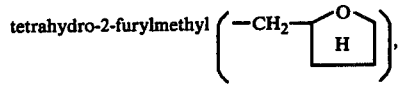, tetrahydro-2-pyranylmethyl 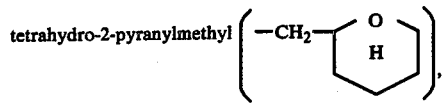, 2-thiophenemethyl 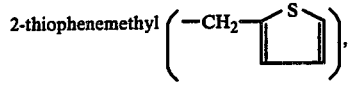, 2,3-dihydrobenzodioxin-2-ylmethyl 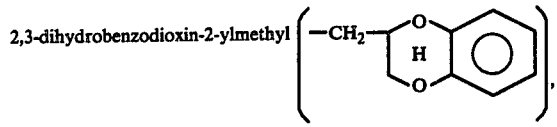, or 2,2-dimethyl-1,3-dioxolan-4-ylmethyl 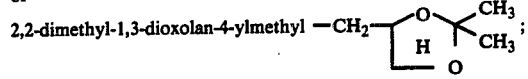;

each R' independently represents hydrogen or methyl; $R^2$ represents hydrogen, alkyl of 1 to 4 carbon atoms or phenyl; $R^3$ represents hydrogen or alkyl of 1 to 4 carbon atoms; and each n independently represents an integer of from 1 to 12.

2. A compound as defined in claim 1 wherein Y is trichloromethyl.

3. A compound as defined in claim 2 wherein X is chloro.

4. A compound as defined in claim 2 wherein X is alkoxy of 1 to 4 carbon atoms.

5. A compound as defined in claim 2 wherein X is OR.

6. The compound as defined in claim 3 which is 2-chloro-6-(2-methoxyethoxy)-4-(trichloromethyl)pyridine.

7. The compound as defined in claim 3 which is 2-chloro-6-(2-ethoxyethoxy)-4-(trichloromethyl)pyridine.

8. The compound as defined in claim 3 which is 2-chloro-6-(2-furanylmethoxy)-4-(trichloromethyl)pyridine.

9. The compound as defined in claim 3 which is 2-chloro-6-(tetrahydro-2-furanylmethoxy)-4-(trichloromethyl)pyridine.

10. The compound as defined in claim 4 which is 2-methoxy-6-(2-methoxyethoxy)-4-(trichloromethyl)pyridine.

11. The compound as defined in claim 5 which is 2,6-bis(2-(methoxyethoxy)-4-(trichloromethyl)pyridine.

12. A fungicidal composition comprising a fungicidally effective amount of a compound corresponding to the formula:

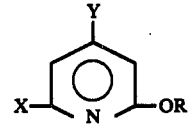

wherein Y represents trichloromethyl, dichloromethyl or dichlorofluoromethyl; X represents chloro, bromo, fluoro, alkoxy of 1 to 4 carbon atoms or OR; R represents:

—(CH₂)₃OR²,

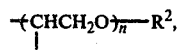

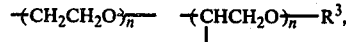

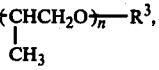

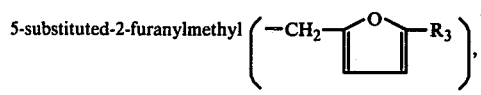

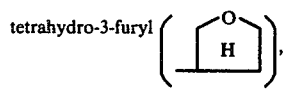

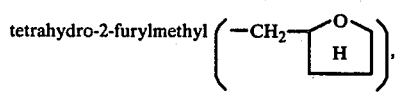

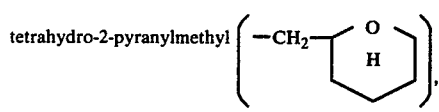

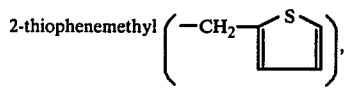

or

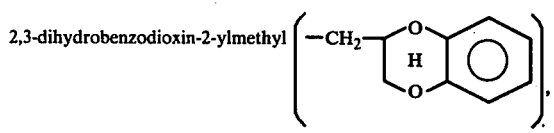

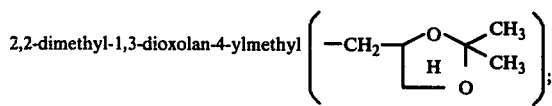

each R' independently represents hydrogen or methyl; $R^2$ represents hydrogen, alkyl of 1 to 4 carbon atoms or phenyl; $R^3$ represents hydrogen or alkyl of 1 to 4 carbon atoms; and each n independently represents an integer of from 1 to 12, in intimate admixture with an inert adjuvant therefor.

13. A composition as defined in claim 12 wherein Y is trichloromethyl.

14. A composition as defined in claim 13 wherein X is chloro.

15. A composition as defined in claim 13 wherein X is alkoxy of 1 to 4 carbon atoms.

16. A composition as defined in claim 13 wherein X is OR.

17. The composition as defined in claim 14 wherein the compound is 2-chloro-6-(2-methoxyethoxy)-4-(trichloromethyl)pyridine.

18. The composition as defined in claim 14 wherein the compound is 2-chloro-6-(2-ethoxyethoxy)-4-(trichloromethyl)pyridine.

19. The composition as defined in claim 14 wherein the compound is 2-chloro-6-(2-furanylmethoxy)-4-(trichloromethyl)pyridine.

20. The composition as defined in claim 14 wherein the compound is 2-chloro-6-(tetrahydro-2-furanylmethoxy)-4-(trichloromethyl)pyridine.

21. The composition as defined in claim 15 wherein the compound is 2-methoxy-6-(2-methoxyethoxy)-4-(trichloromethyl)pyridine.

22. The compound as defined in claim 16 wherein the compound is 2,6-bis(2-methoxyethoxy)-4-trichloromethyl)pryidine.

23. A method for protecting plants from plant fungal disease organisms which attack the plant root system which comprises contacting plants, plant parts or their habitat with a non-phytotoxic, plant protecting amount of a plant protectant corresponding to the formula:

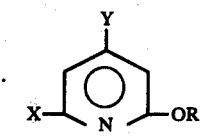

wherein Y represents trichloromethyl, dichloromethyl or dichlorofluoromethyl; X represents chloro, bromo, fluoro, alkoxy of 1 to 4 carbon atoms or OR; R represents:

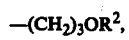

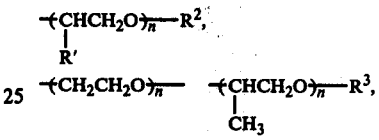

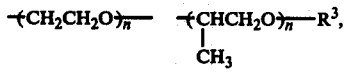

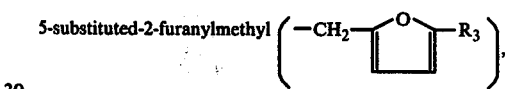

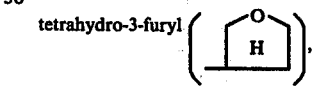

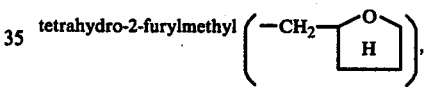

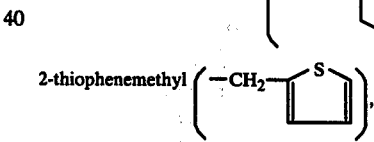

or

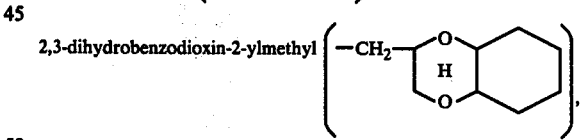

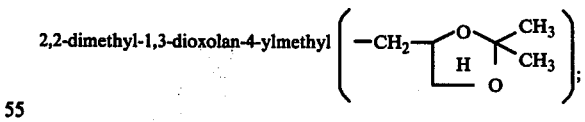

each R' independently represents hydrogen or methyl; $R^2$ represents hydrogen, alkyl of 1 to 4 carbon atoms or phenyl; $R^3$ represents hydrogen or alkyl of 1 to 4 carbon atoms; and each n independently represents an integer of from 1 to 12, in intimate admixture with an inert adjuvant therefor.

24. The method as defined in claim 23 wherein the plants, plant parts or habitat are contacted with the plant protector prior to the plants being attacked by plant root disease organisms.

25. The method as defined in claim 23 wherein the plants, plant parts or habitat are contacted with the plant protector after the plants have been attacked by plant root disease organisms.

26. The method as defined in claim 23 wherein the plant roots are contacted with the plant protectant.

27. The method as defined in claim 23 wherein the above-ground portions of the plants are contacted with the plant protectant.

28. The method as defined in claim 23 wherein plant seeds are contacted with the plant protectant.

29. A method as defined in claim 23 wherein Y is trichloromethyl.

30. A method as defined in claim 29 wherein X is chloro.

31. A method as defined in claim 29 wherein X is alkoxy of 1 to 4 carbon atoms.

32. A method as defined in claim 29 wherein X is OR.

33. The method as defined in claim 30 wherein the plant protectant is 2-chloro-6-(2-methoxyethoxy)-4-(trichloromethyl)pyridine.

34. The method as defined in claim 30 wherein the plant protectant is 2-chloro-6-(2-ethoxyethoxy)-4-(trichloromethyl)pyridine.

35. The method as defined in claim 30 wherein the plant protectant is 2-chloro-6-(2-furanylmethoxy)-4-(trichloromethyl)pyridine.

36. The method as defined in claim 30 wherein the plant protectant is 2-chloro-6-(tetrahydro-2-furanylmethoxy)-4-(trichloromethyl)pyridine.

37. The method as defined in claim 31 wherein the plant protectant is 2-methoxy-6-(2-methoxyethoxy)-4-(trichloromethyl)pyridine.

38. The method as defined in claim 32 wherein the plant protectant is 2,6-bis(2-methoxyethoxy)-4-(trichloromethyl)pyridine.

* * * * *